US005665589A

United States Patent [19]
Harris et al.

[11] Patent Number: 5,665,589
[45] Date of Patent: *Sep. 9, 1997

[54] HUMAN LIVER EPITHELIAL CELL LINES

[75] Inventors: Curtis C. Harris, Bethesda; Katharine H. Cole, Dayton, both of Md.; John F. Lechner, Albuquerque, N. Mex.; Roger Reddel, St. Ives, Australia

[73] Assignee: The United States of America as represented by the Department of Health and Human Services, Washington, D.C.

[*] Notice: The term of this patent shall not extend beyond the expiration date of Pat. No. 5,506,131 and 5,529,920.

[21] Appl. No.: 25,336

[22] Filed: Mar. 3, 1993

Related U.S. Application Data

[63] Continuation-in-part of Ser. No. 879,165, May 1, 1992, Pat. No. 5,529,920, which is a continuation of Ser. No. 377,967, Jul. 11, 1989, abandoned, which is a continuation-in-part of Ser. No. 284,368, Dec. 14, 1988, abandoned, and Ser. No. 284,331, Dec. 14, 1988, abandoned.

[51] Int. Cl.$^6$ ............... C12N 5/06; C12N 5/10
[52] U.S. Cl. ............... 435/370; 435/70.1; 435/172.3; 435/320.1; 435/371; 935/71
[58] Field of Search ............... 435/320.1, 240.2, 435/240.1, 240.21, 240.3, 240.31, 6, 7.21, 70.1; 935/71

[56] References Cited

U.S. PATENT DOCUMENTS

| | | | |
|---|---|---|---|
| 4,393,133 | 7/1983 | Knowles et al. | 435/6 |
| 4,558,004 | 12/1985 | Hammock et al. | 435/4 |
| 5,506,131 | 4/1996 | Harris et al. | 435/240.2 |
| 5,529,920 | 6/1996 | Cole et al. | 435/240.2 |

FOREIGN PATENT DOCUMENTS 8103663   6/1981   WIPO .

OTHER PUBLICATIONS

Woodworth et al, Cancer Research 46:4018–4026, Aug. 1986.
Ledley et al, Proc. Natl. Acad. Sci., vol. 84: 5335–5339 (1987).
Kaighn et al, Proc. Natl. Acad. Sci., vol. 68: 2396–2400 (1971).
Lechner et al, Cancer Detect. and Prevention, vol. 14: 239–244 (1989).
Ballet et al, Hepatology, vol. 4: 849–854 (1984).
Chessebeuf et al, In Vitro, vol. 20, No. 10: 780–795 (1984).
Cruise et al, J. of Cell. Phys., vol. 125: 45–50 (1985).
Luetteke et al, "Control of Hepatocyte Prolif. in Vitro," 93–118, in The Isolated Hepatocyte, Acad. Press, 1987.
Salas–Prato et al, In Vitro Cell. & Develop. Bio. 24, No. 3 (1988).
Strom et al, "Genotoxicity Studies w/Human Hepatocytes," 1987 in The Isolated Hepatocyte, Academic Press, 1987.
Sells et al, In Vitro Cell. & Develop. Bio. 21, No. 4 (1985).
Nancy L. R. Bucher, "Regulation of Liver Growth: Historical Perspectives and Future Directions," (1987), in The Isolated Hepatocyte, Academic Press.
Steinberg et al., 1983. The Journal of Investigative Dematology, vol. 81, No. 1 Supplement, pp. 131 S–136 S.
Pfeifer, Cole, Smoot, et al.; *Simian Virus 40 Large Tumor . . . ;* Nat'l. Acad. of Sci.; (1993); pp. 5123–5127.
Cole, Jones Lipsky, et al.; *Comparative Effects of Three Carcinogens . . . ;* Carcinogenesis; (1989); vol. 10, No. 1; pp. 139–143.
Chemical Abstracts; vol. 117; (1992); pp. 318–319, Abstr. 42502e.
Miyazaki, Mihara, Bai, et al.; *Immortalization of Epithelial–Like Cells . . . ;* Exp. Cell Res.; (1993); vol. 206; pp. 27–35.
Hering, Griffin & Strauss; *Immortalization of Human Fetal Sinusoidal Liver Cells . . . ;* Exp. Cell Res.; (1991); vol. 195; pp. 1–7.
Hsu, Harris, Lipsky, et al.; *Cell and Species Differences . . . ;* Mutation Res.; (1986); vol. 177, No. 1; pp. 1–7.
Groopman, DeMatos, et al.; *Molecular Dosimetry of Urinary Aflatoxin . . . ;* Carcinogenesis; vol. 13, No. 1; pp. 101–106.

*Primary Examiner*—Brian R. Stanton
*Attorney, Agent, or Firm*—Birch, Stewart, Kolasch & Birch, LLP

[57] ABSTRACT

Immortalized cell lines derived from normal adult human liver are described which express phenotypic characteristics of normal adult liver epithelial cells.

15 Claims, 7 Drawing Sheets

HUMAN LIVER EPITHELIAL CELL LINES

RELATED APPLICATIONS

This application is a Continuation-In-Part of U.S. patent application Ser. No. 07/879,165, filed May 1, 1992, now U.S. Pat. No. 5,529,920, which is a Continuation application of U.S. patent application Ser. No. 07/377,967, filed Jul. 11, 1989, and now abandoned, which is a Continuation-In-Part application of Ser. No. 07/284,368, filed Dec. 14, 1988 and now abandoned, and also of Ser. No. 07/284,331, filed Dec. 14, 1988 and now abandoned, all of which are hereby incorporated in their entirety by reference.

BACKGROUND OF THE INVENTION

1. Field of the Invention

The invention relates to continuous cell lines derived from normal adult human liver tissue. These cell lines display morphological and gene expression characteristics consistent with parentage of normal human hepatocytes. The cell lines are immortalized by expression of the large T antigen (TAg) of the SV40 virus, but are not tumorigenic. As such, they provide a reproducible source of cells for studies of initiation and progression of carcinogenesis, especially chemical and viral carcinogenesis caused by liver metabolism of non-tumorigenic precursor compounds to genotoxic substances or by infection by oncogenic hepatitis viruses.

2. Description of the Related Art

Throughout this patent application, numerous articles of the scientific literature are cited. Each of these references is hereby incorporated in its entirety by such citation.

Kaighn and Prince (1) described clonally-derived cultures of liver cells from fetal, infant and adult human donors more than 20 years ago. These cultures all had limited lifespans. Their observations suggested the existence of normal adult human liver epithelial cells that are either less differentiated, or are capable of undergoing retrograde differentiation into a form that is capable of completing a few population doublings in vitro if cultured under appropriate conditions. Cultures of rat liver epithelial cells have been established (2,3), but these cultures, like those of Kaighn and Prince, have only limited life span. Recently, we described a serum-free culture medium (LCM, described below) which supports extended replication of normal human liver epithelial cells (4). However, the growth potential of liver cells on this medium was still limited, that is, no more than 12 rounds of cell division were ever obtained in any of our cultures. All of these cultures are not suitable for long-term studies due to their limited lifespan.

Metabolic activation of environmental carcinogens from several chemical classes have been studied in human liver tissue explants or microsomes and isolated human hepatocytes. (5). Furthermore, observed animal species-specific differences in aflatoxin $B_1$ ($AFB_1$) and 2-acetylaminofluorene metabolism indicate the need for studying human liver or hepatocytes. However, because tissue availability is limited, individuals vary in their propensity for xenobiotic metabolism and reproducible in vitro conditions are difficult to establish, a reproducible system with human liver cells for pharmaco-toxicological studies has not been established.

Several groups of investigators have reported that the longevity of cultures of human epithelial cells can be increased or in some cases made indefinite (5,6) by transformation with the SV40 virus large T antigen (TAg) gene. Such transformed cells may have near normal karyotype and some of the isolates retain many of the growth and differentiation characteristics of their normal counterparts, including non-tumorigenicity. In addition, Woodworth et al. and Ledley et al. (7–9) have reported that rat hepatocytes transformed with an SV40 TAg gene retained several normal hepatocyte characteristics. Unfortunately, such cultures are not useful for studies of human carcinogenesis and drug metabolism studies, since metabolism of xenobiotic compounds can be very different in humans and in rats.

SUMMARY OF THE INVENTION

The human liver is one of the few organs in adults that is capable of regeneration. However, no continuously replicating culture of non-neoplastic, adult human hepatocytes has ever been established. We disclose herein the establishment of a continuous culture of normal human liver epithelial cells (hepatocytes) by infection of replicative cultures of such cells with a retroviral vector containing the SV40 TAg gene. These cell lines (THLE cells) overcome the deficiencies of previous cell lines with regard to limitation of lifespan or non-human origin and so provide a reproducible source of cells for long-term studies of human carcinogenesis and toxicology. The cells appear to be immortal, that is, they have an indefinite lifespan in vitro. Cells of the lines described herein are non-tumorigenic and thus provide a resource for studies of processes by which cells are made tumorigenic. They are particularly valuable in the study of chemical carcinogenesis, as metabolism of non-carcinogenic precursor compounds by liver enzymes to a genotoxic compound is thought to be a major mechanism of carcinogenesis by chemicals. Thus the cells provide a means of screening chemicals for carcinogenic potential by exposure of the cells to the suspect carcinogen precursor and assay for conversion of the cells to a tumorigenic phenotype. Reproducibility of such an assay depends upon having a reproducible cell line to carry out the tests upon. The THLE cell lines of the present invention provide such reproducible cell lines.

Furthermore, the THLE cells of the present invention might prove useful in the investigation of the control of differentiation processes. It is generally thought that proliferation and differentiation are opposing cellular processes (47,48). Thus, the THLE cells can be used to identify drugs useful in the treatment of liver tumors by investigating the effect of such drugs upon the phenotype of the THLE cells. Compounds which induce terminal differentiation of the THLE cells would be considered to be promising candidates.

The introduction of oncogenes in addition to the SV40 TAg gene can also be performed on the THLE cells so as to investigate the effect of the expression of such additional oncogenes upon the tumorigenicity or other phenotypic aspect of the THLE cells. Again, the cell lines so derived can be used as target in screening assays for compounds which are effective to stop the proliferation of cells expressing these additional oncogenes.

Finally, hepatocytes are the cell type infected by hepatitis viruses (HepA, HepB, HepC and nonA-nonB hepatitis) and also the cell type infected by many human parasites. Thus THLE cells provide an in vitro host for the growth of these organisms and consequently an in vitro system for study of the cell biology of such infections and screening of compounds for efficacy in blocking or curing such infections.

DETAILED DESCRIPTION OF THE INVENTION

Figure 1A:
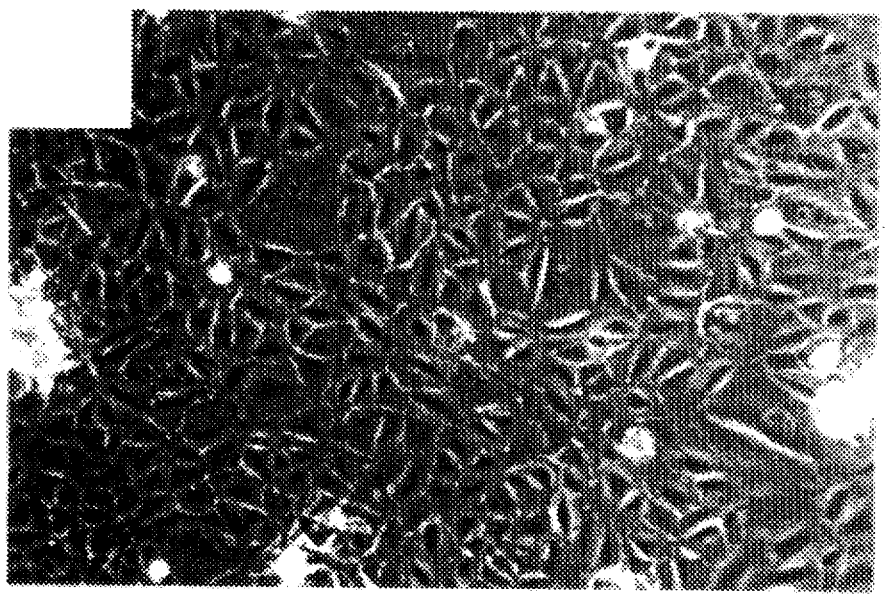
FIGS. 1A–D show the morphology and expression of cellular markers in THLE-2 cells; Phase-contrast micrograph showing the epithelial appearance of THLE-2 cells (A), Indirect Immunofluorescence staining for SV40 T-antigen (B) and cytokeratin 18 (C) demonstrating the presence of both proteins in nearly 100% of passage 5 cells, Immunoperoxidase staining showing clonal expression of albumin in THLE-2 cells of passage 5 (D). For immunofluorescence analyses, non-specific binding was blocked with the appropriate blocking serum (1:100 dilution, 20 min.). Subsequently, antibodies (IgG) specific for albumin (1:20; American Qualox, La Mirada, Calif.), general cytokeratins (1:15; ICN, Costa Mesa, Calif.), cytokeratin 18 cytokeratin 19 (1:20 each; ICN, Costa Mesa, Calif.), α-fetoprotein (1:50; Zymed, San Francisco, Calif.), $\alpha_1$-antitrypsin, $\alpha_2$-macroglobulin (1:50; Chemicon, Inc., Temecula, Calif.) and SV40 T-antigen (1:5; Oncogene Science, Manhasset, N.Y.), were incubated at room temperature (30 min to 1 hr) and developed with fluorescent secondary antibodies diluted 1:32 at room temperature (1 hr.) Immunocytochemical staining for albumin was performed by incubation with a secondary rabbit anti-mouse; DakoCorp, Santa Barbara, Calif.) and tertiary (swine anti-rabbit; DakoCorp, Santa Barbara, Calif.) antibodies and development with horse radish peroxidase at room temperature (30 min each incubation).
Figure 1B:
Figure 1C:
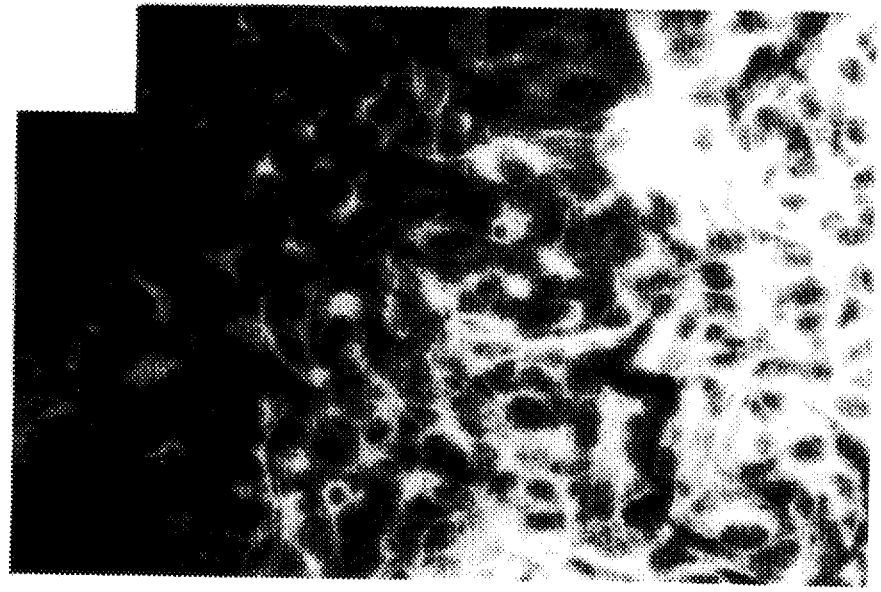
Figure 1D:
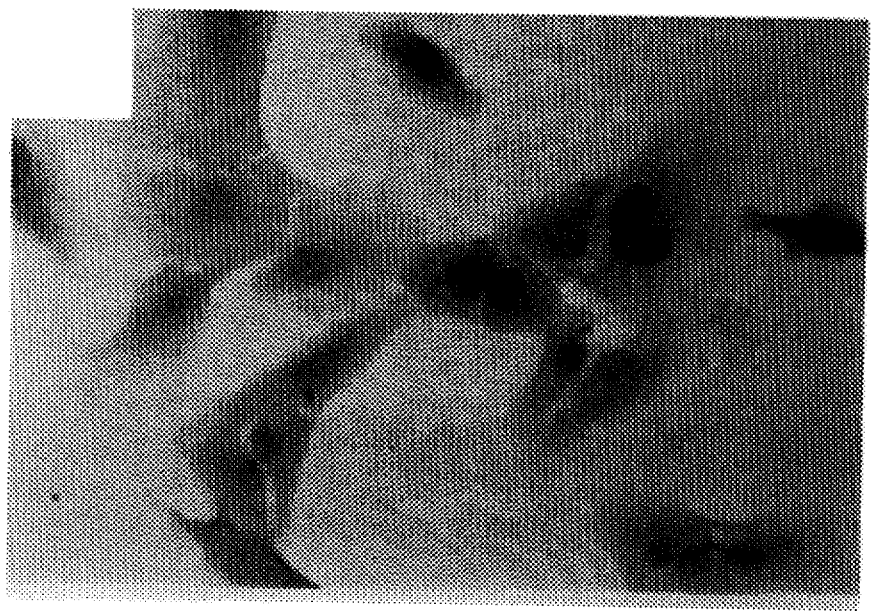

The cell lines of the present invention provide reproducible biological materials for investigations in carcinogenesis and toxicology. The cells can be used for investigations of metabolic activation of compounds to cytotoxins or carcinogens. The cells may be used in their present state, or alternatively, exogenous genes in addition to SV40 T antigen can be introduced into the cells. Similarly, the cell lines of the present invention can be infected with various viruses of interest in human disease, such as hepatitis.

Genes of interest in studies of carcinogenesis and toxicology, for example, might be oncogenes per se, wild-type or mutated tumor suppressor genes or genes encoding enzymes for metabolism of xenobiotic compounds. A family of particularly interesting genes are mutants of the tumor suppressor gene p53, which have been implicated in the progression of a variety of tumor types.

The cell lines of the present invention, either as described herein or containing additional exogenous genes, are useful in the screening and study of the mode of action of therapeutic compounds which alter gene expression in the cells or which alter the toxicologic effects of some second substance.

Preferred embodiments of the invention are described by means of the examples below. These examples are expressly meant to illustrate, rather than limit, the scope of the invention.

Cell proliferation is measured in a variety of the experiments described below. Thus, the methods used for such measurement are set forth as general methods. DNA synthesis is measured in cells inoculated at clonal density (100 cells/cm$^2$). The medium is changed to fresh medium the next day and after two additional days of incubation [$^3$H]-thymidine (New England Nuclear) is added to the cell cultures at 0.5 μCi/ml. Twenty-four hours later the acid precipitable fraction is collected on glass fiber filters and the amount of [$^3$H] incorporated is quantified by scintillation counting. Alternatively, proliferation is measured by counting the number of cells in each colony. Medium is changed to the medium in which proliferation is to be assayed one day following inoculation at clonal density and the dishes are incubated for a further 7 days. The cells are then formalin fixed and stained with crystal violet. The number of cells per colony is determined and the population doublings per day is calculated as previously described (13).

For many of the experiments described, for example Southern and Northern blot analyses and metabolic experiments, cultures are grown to high density. Such cultures are incubated in T175 tissue culture flasks or in 800 ml roller bottles and grown to a density of $3.7 \times 10^4$ cells/cm$^2$.

EXAMPLE 1

Establishment of Continuous Cultures of Normal Adult Human Liver Epithelial Cells (THLE Cells)

i) Primary culture of normal adult liver tissue

LCM medium (4) consists of PFMR-4 medium (Biofluids, Rockville, Md.) wherein the Ca$^{2+}$ concentration is reduced to 0.4 mM and arginine is replaced with 0.3 mM ornithine, supplemented with insulin (1.45 μM), transferrin (125 nM), cholera toxin (300 pM), epidermal growth factor (825 pM), hydrocortisone (0.2 μM), triiodothyronine (10 nM), retinoic acid (10 nM), phosphoethanolamine (0.5 μM), Ex-Cyte V (312 μM), bovine pituitary extract (ref. 10, 7.5 μg protein/ml), and chemically denatured serum (10).

To make LCM medium conditioned by Hep-G2 cells (HGLCM), Hep-G2 cells (American Type Culture Collection, Rockville, Md.) are maintained in DMEM medium supplemented with 10% fetal bovine serum. Near-confluent cultures of such cells are washed twice with LCM and then maintained in LCM for 72 hours. The supernatant medium (HGLCM) is removed, sterilized by filtration through a 0.22 μm membrane and stored under sterile conditions.

Normal liver epithelial cells are obtained by collagenase/dispase perfusion of the left lower lobe of livers from immediate autopsy of adult donors with no clinical evidence of cancer (11). Cultures are inoculated into flasks that have been pre-coated with collagen I (Vitrogen™, Celtrix Laboratories, Palo Alto, Calif.) and incubated overnight in Waymouth's medium containing 10% fetal bovine serum. The following day, the cultures are rinsed with phosphate buffered saline (PBS) and the medium is changed to HGLCM.

Within 2 to 4 days of isolation of the normal cells, groups of randomly spaced replicating cells with an epithelial-like morphology are evident. These cultures form a confluent monolayer after 10–14 days of incubation. These normal cells can be subcultured at a 1:4 split ratio using the same collagenase/dispase solution as is used in establishing the primary culture to remove the cells from the surface of the culture vessel. The average lifespan of these normal liver epithelial cell cultures is 12 population doublings.

ii) Production of the SV40 TAg-expressing retrovirus

A recombinant retrovirus carrying the large T antigen gene of SV40 virus is constructed by insertion of BglI-HpaI fragment of the SV40 viral DNA (nucleotides 5235–2666) into the BamHI site of the pZipNeoSVX (12) retroviral vector, using BamHI linkers and standard recombinant DNA techniques. The fragment of the SV40 genome employed lacks both the early promoter and the polyadenylation site.

Infectious recombinant virus particles are made by transfecting the amphotropic packaging cell line PA317 with the ecotropic recombinant vector obtained above. Transfected cells are isolated by neomycin selection and 10 clones are isolated. The cloned PA317 cells are propagated in DMEM medium supplemented with 10% FBS. The medium is changed to serum-free PC-1 medium (Ventrex Laboratories, Portland, Me.) and virus is titered by infecting $8 \times 10^4$ NIH 3T3 cells in a 60 mm dish with various dilutions of the supernatant medium containing virus in the presence of 8 μg/ml polybrene and counting the colonies after 10 days of selection using 750 μg/ml of neomycin.

iii) Infection of primary liver tissue culture cells

A pool of virus from 7 of the 10 clones of the transfected PA317 cells is used to infect the primary liver tissue cultures. $8 \times 10^4$ cells of the primary cultures were infected with 0.1 pfu of the recombinant virus for 2 hours in the presence of 8 μg/ml polybrene in PC-1 medium. After the infection, the cultures are washed with HEPES buffered saline (HBS) and incubated in LCM medium. Infection with the recombinant virus causes virtually all of the liver cells in the culture to undergo rapid division. Several cultures have been so established. Of these, THLE-2 and THLE-3 are passaged as mass cultures. Initially, the THLE-2 and THLE-3 cells undergo approximately 25 population doublings during the first six weeks post-infection, then growth decreases markedly. Cells are cryopreserved at each passage during this early growth period.

The THLE-2 cell line was deposited under the terms of the Budapest Treaty at the American Type Culture Collection, 12301 Parklawn Dr., Rockville, Md., on May 16, 1989 and assigned the accession number CRL 10149. The THLE-3 cell line was deposited under the terms and conditions of the Budapest Treat at the American Type Culture Collection on Jan. 14, 1993 and was assigned the accession number CRL 11233.

THLE-2 cells from such early passage cryopreserved stocks are used to determine the growth responses of the cells to the various supplements of the LCM medium. Single elimination experiments show that the clonal growth rate of the early passage THLE-2 cells is increased by omitting the Ex-Cyte V and cholera toxin from the LCM and also by replacing the ornithine with arginine. Use of medium conditioned by THLE-2 cells rather than by HepG2 cells further improves the growth of the THLE-2 cells. Modified LCM (MLCM) medium is thus LCM reformulated by the omission of Ex-Cyte V and cholera toxin and using arginine rather than ornithine (at 0.3 mM) and adding to 30% of the volume medium conditioned by THLE-2 cells rather than by HepG2 cells.

Using MLCM to maintain the culture, THLE-2 cells have been cultured for more than 130 population doublings with no evidence of senescence. The apparent maximal clonal growth generation time is 24 hours and their colony forming efficiency averages 15%. THLE-3 cells were switched to MLCM at early passage and consequently this cell line never entered a quiescent stage. THLE-3 cells have been grown for more than 100 population doublings. Their growth rate is 0.7 PDL/day and their colony forming efficiency is 15%.

EXAMPLE 2

Analysis of Liver-specific Gene Expression in THLE Cells

The THLE cells were evaluated for expression of a number of liver-specific genes at both the transcriptional and translational levels.

Karyotype analysis is performed using techniques standard in the art.

For Southern blot analysis, cellular DNA is extracted by methods typical in the art and digested with ClaI restriction enzyme. The DNA is electrophoresed on a 0.7% agarose gel and transferred to Gene Screen Plus™ (DuPont, Wilmington, Del.). Genomic DNA is analyzed for the presence of SV40 T-antigen DNA by probing with the 1.17 kilobasepair (kb) HindIII fragment of the large T-antigen gene labelled with $^{32}$p by use of a nick translation kit according to the method described by the manufacturer (DuPont).

mRNA expression is assessed by both Northern blot analysis and by in situ hybridization. For Northern blotting, RNA is isolated as previously described (15) by hybridization to biotinylated oligo-dT followed by capture of the hybridized RNA with streptavidin paramagnetic beads (Promega, Madison, Wis.). The hybridization protocol has also been previously described (15).

For in situ hybridization, cells are incubated for 10 days in culture chamber slides, then washed twice with PBS (pH 7.4) and fixed for 3 minutes in PBS containing 4% paraformaldehyde, 2% sucrose, 5 mM $MgCl_2$ and 0.02% diethyl pyrocarbonate. The slides are then washed with two changes of PBS containing 5 mM $MgCl_2$ and then incubated for 10 minutes in 0.1M glycine/0.2M Tris and subsequently acetylated by 10 minutes incubation in 5% acetic anhydride/ 0.1M triethanolamine, pH 8.0. The slides are then washed in PBS and prehybridized in 50% formamide, 2×SSC, 10 mM dithiothreitol (DTT) at 52° C. for 10 minutes. Hybridization is performed at 50° C. using cRNA probes or 42° C. using cDNA probes in 50% formamide, 2×SSC, 0.1M DTT, 1 mg/ml tRNA, 10 mg/ml sonicated salmon sperm DNA, 2 mg/ml bovine serum albumin (BSA) and $6 \times 10^4$ cpm/µl of probe. Following hybridization, slides probed with cRNA are rinsed in 50% formamide, 5×SSC, at 50° C. for one hour, then RNAse digested as described by Maier et al. (16). The slides are then washed at 45° C. in 50% formamide, 2×SSC for 30 minutes and finally in 2×SSC for 30 minutes at 45° C. Slides probed with cDNA probes are rinsed in 50% formamide, 2×SSC at 37° C. for 30 minutes, then in 50% formamide, 1×SSC at room temperature and finally in 1×SSC at room temperature. Hybridized slides are then autoradiographed using NBT2 emulsion (Eastman Kodak), exposed at 4° C. for 7 to 10 days and developed with Kodak D19 developer, then counterstained with hematoxylin and eosin, dehydrated and mounted with Permount.

cDNA probes are labelled by nick translation using $^{35}$S dCTP as substrate. The average length of such probes is 0.2 kb. Riboprobes (cRNA) are prepared by the transcription protocol of Melton et al. (17) using $^{35}$S UTP as the labelled nucleotide. The transcripts are then partially hydrolyzed with alkali so that most of the label is in fragments 100–200 nucleotides long.

The presence of epoxide hydrolase is determined in the cell lines by hybridization with a human gene probe; either the SmaI-XhoI (0.4 kb) or the NcoI-NspI (0.9 kb) fragments of the plasmid R60 (Oxford Biochemicals, Oxford, Mich. 48051). NADPH cytochrome p450 reductase probe is derived from plasmid hp450 (F. Gonzales, National Cancer Institute, National Institutes of Health, Bethesda, Md.) by EcoRI digestion and isolation of the 2.4 kb fragment. Superoxide dismutase (SOD) expression is determined by hybridization to a 0.45 kb EcoRI-HindIII fragment of the human cDNA obtained from the plasmid sp65/SOD (18). Glutathione peroxidase is analyzed by use of a 0.8 kb EcoRI fragment of the human cDNA obtained from the plasmid pSPT19/GPX (19). Expression of Glutathione-S-transferase πi, α and µ are assessed by hybridization with the 0.73 kb EcoRI fragment of plasmid pGEM4/GSTπi (J. A. Moxow, National Cancer Institute, National Institutes of Health, Bethesda, Md.), to the 0.7 kb EcoRI fragment of plasmid pGST2-PvuII (20) and to the 0.67 kb PstI-EcoRI fragment of the plasmid pGST-T-Nco (gift of P. G. Board, Australian National University), respectively. Probe for albumin mRNA is isolated from plasmid B44 (21). The 0.73 kb insert cDNA of B44 is subcloned in pGEM4 (Promega, Madison, Wis.) between the PstI and HindIII sites. For detection of catalase mRNA, nick-translated probe is prepared from the 1.25 kb EcoRI-HindIII fragment of a plasmid containing the HindIII-PvuII fragment of the human catalase cDNA (22). Probes for cytochrome p450 isoenzymes correspond to the 1.0 kb 3' EcoRI 1A2, 1.0 kb 3' EcoRI 1A1, 1.3 kb 3' BamHI-EcoRI IIA3, the 3' 1.6 kb BamHI-EcoRI IIE1, the 1.1 kb 3' EcoRI IIIA4, the 0.8 kb 5' EcoRI IIB1 cDNA fragment or the entire 1.6 kb IID6 cDNA isolated by EcoRI digestion of plasmids provided by F. Gonzales (National Cancer Institute, National Institutes of Health, Bethesda, Md.).

For immunocytochemistry, cells are grown to near confluence on glass chamber slides (Lab-Tek) and rinsed in phosphate-buffered saline (PBS). The cells are fixed by immersion of the slides in phosphate buffer containing paraformaldehyde (for albumin staining) or 100% methanol at 4° C. (for cytokeratin and TAg staining). The slides are then rinsed in PBS and the appropriate blocking serum (1:100 dilution) is placed on each slide for 20 minutes. The primary antibodies (IgG) against albumin (1:20 dilution, ICN, Costa Mesa, Calif.), general cytokeratins (1:15 dilution, ICN), cytokeratin 18 and cytokeratin 19 (each at 1:20 dilution, ICN) and SV40 T-antigen (1:5 dilution, Oncogene Science, Manhasset, N.Y.) are applied to the slides and incubated for 30 minutes to 1 hour at room temperature. The slides are rinsed in PBS to remove unbound antibody. For immunofluorescence studies, fluorescein isothiocyanate or tetramethyl rhodamine isothiocyanate labelled secondary antibodies are placed on the slides for 1 hour at room temperature. For staining with horseradish peroxidase (HRP) the slides are incubated with swine anti-mouse secondary antibody for 30 minutes at room temperature, rinsed in PBS and then incubated with HRP-linked rabbit anti-swine tertiary antibody under the same conditions. HRP is detected by turnover of a benzidine substrate.

For negative control experiments, 3T6 mouse fibroblast cells were used. HepG2 cells were used as a positive control cell line.

Figure 2A:
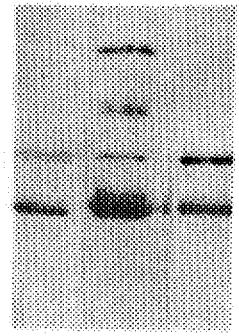
FIGS. 2A and B show albumin secretion of THLE-2 (A) and THLE-3 (B). When normalized by densitometry to the simultaneously immunoprecipitated albumin standard of 3 ng in A and 2 μg in B approximately 300 pg/ml, 70 pg/ml and 14.5 ng/ml albumin were secreted in 24 hrs by THLE-2 (Rb), THLE-2 (FL) and THLE-3 (FL), respectively.
Figure 2B:
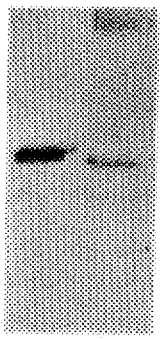
Figure 3A:
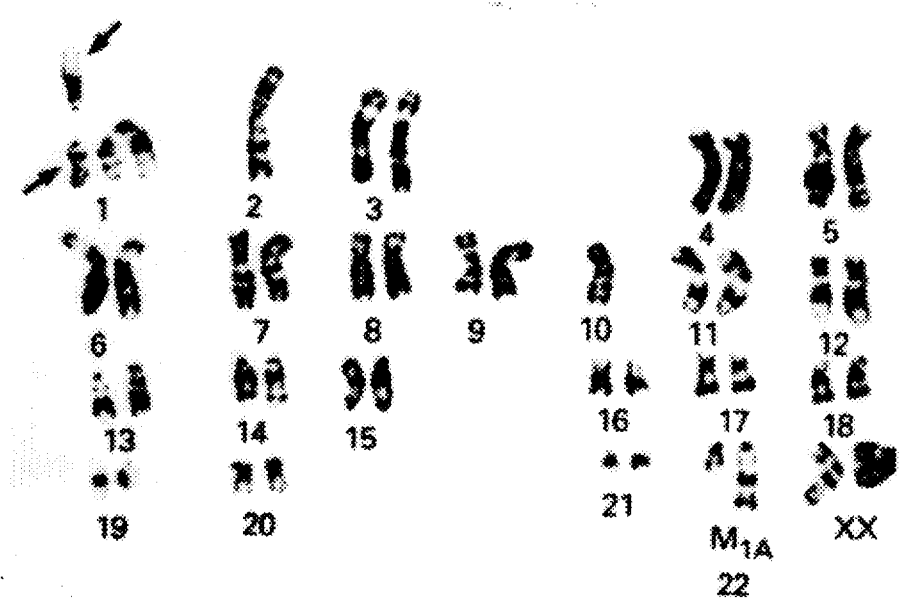
FIGS. 3A and B show karyotypes of THLE-2 and THLE-3. Monosomy of chromosomes 2 and 10, a break of chromosome 1 (arrow) and a 22q+ translocation leading to the marker chromosome $M_{1A}$ characterize the near-diploid metaphase of THLE-2 at passage 18(A). Typical SV40 T antigen effects were also detected in THLE-3 at passage 22(B), illustrated by the monosomy of chromosomes 13 and 22 and deletions in chromosomes 2 and 8. An unidentified marker (M) chromosome is also seen.
Figure 3B:
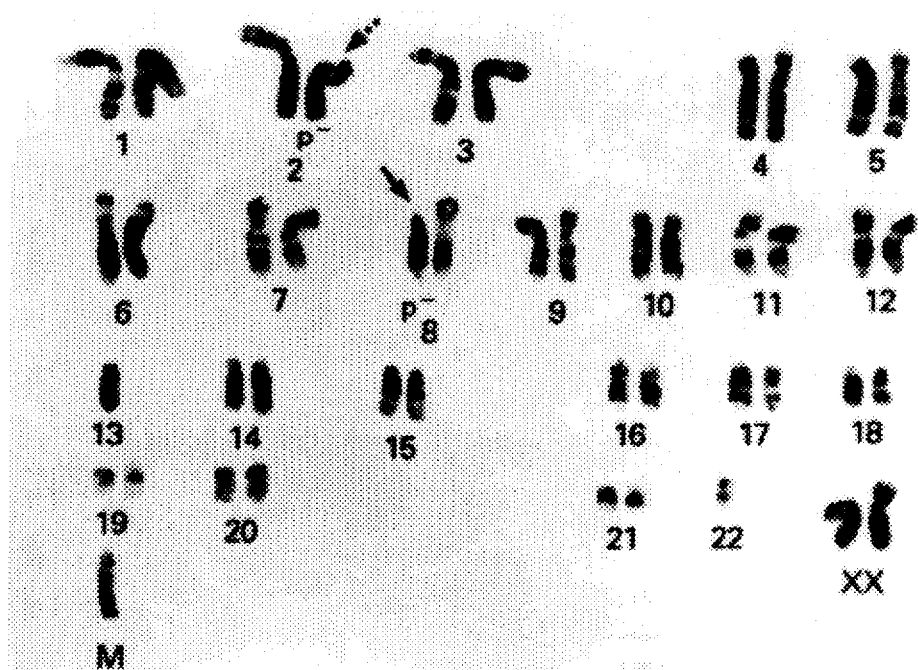
Figure 4A:
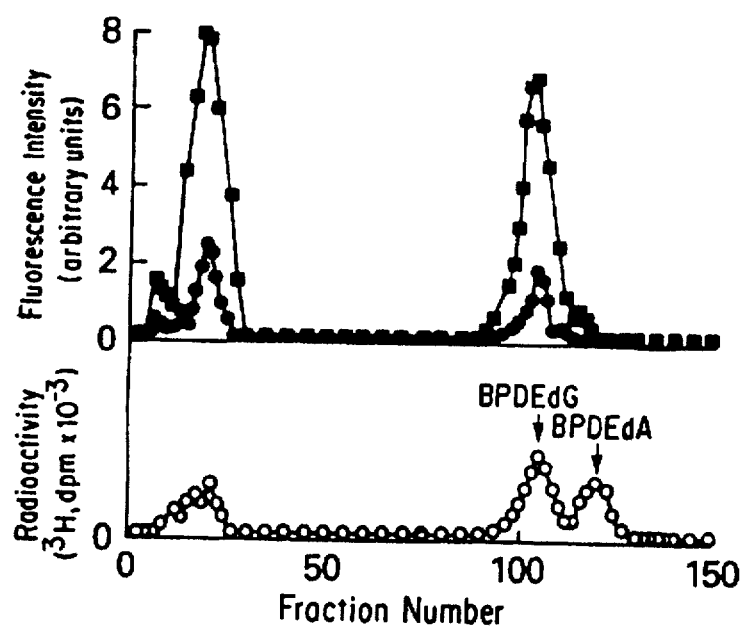
FIGS. 4A-E show the results of an experiment assaying metabolic activation of carcinogens. THLE-2 cells were incubated (24 hrs) with 1.5 μM $^3$H-B[a]p, 32 μM $^3$H-AFB$_1$ or 50 μM DMN, respectively. Pretreatment with Arochlor 1254 was performed 24 hrs before carcinogen treatment. The cells were then harvested with trypsin, suspended in lysis buffer (5–10 ml), (Applied Biosystems, Foster City, Calif.), and treated with ribonuclease and proteinase K (2 hrs each). Carcinogen-modified DNA was isolated from cells by chloroform/phenol extraction (39), hydrolysed and chromatographed. BPDE-DNA adducts were identified by mixing the hydrolysed DNA bases with UV-absorbing quantities of known BPDE-DNA standards and were fractioned on Sephadex LH20 columns and further characterized by HPLC (A; ■, Arochlor induced; ○, uninduced) (24). Northern blot analysis (B) of polyA$^+$-selected mRNA showed an induction of CYP1A1 normalized to GAPDH where Arochlor <B[a]P < Arochlor+B[a]P. The relative CYP1A1/GAPDH ratios are 0.73, 10.0 and 13.1, respectively. Alkyl-DNA adduct analysis was performed by HPLC and detected by $^{32}$P-postlabeling. Autoradiograms of the two-dimensional TLC separation of nucleotide 32P-postlabeling assay of DNA from untreated cells (C) did not show detectable N7-methyl deoxyguanosine adducts, but cells exposed to DMN (D) had detectable levels as demonstrated in this case at 28 fmol per μg DNA. Adducts co-eluted with UV markers of the postlabeled product to confirm adduct identity. The level of adduct was determined through the use of scintillation counting and calibration curves for known versus detected molar ratios of adduct to unmodified dGp. Purified DNA from AFB$_1$-treated cells was assayed by high performance HPLC adduct purification and detection (23). The HPLC-profiles of AFB$_1$-DNA adducts at 24 hrs identified AFB$_1$-fAPyr as the major product (E). Identifications are based on co-elution with authentic standards.
Figure 4E:
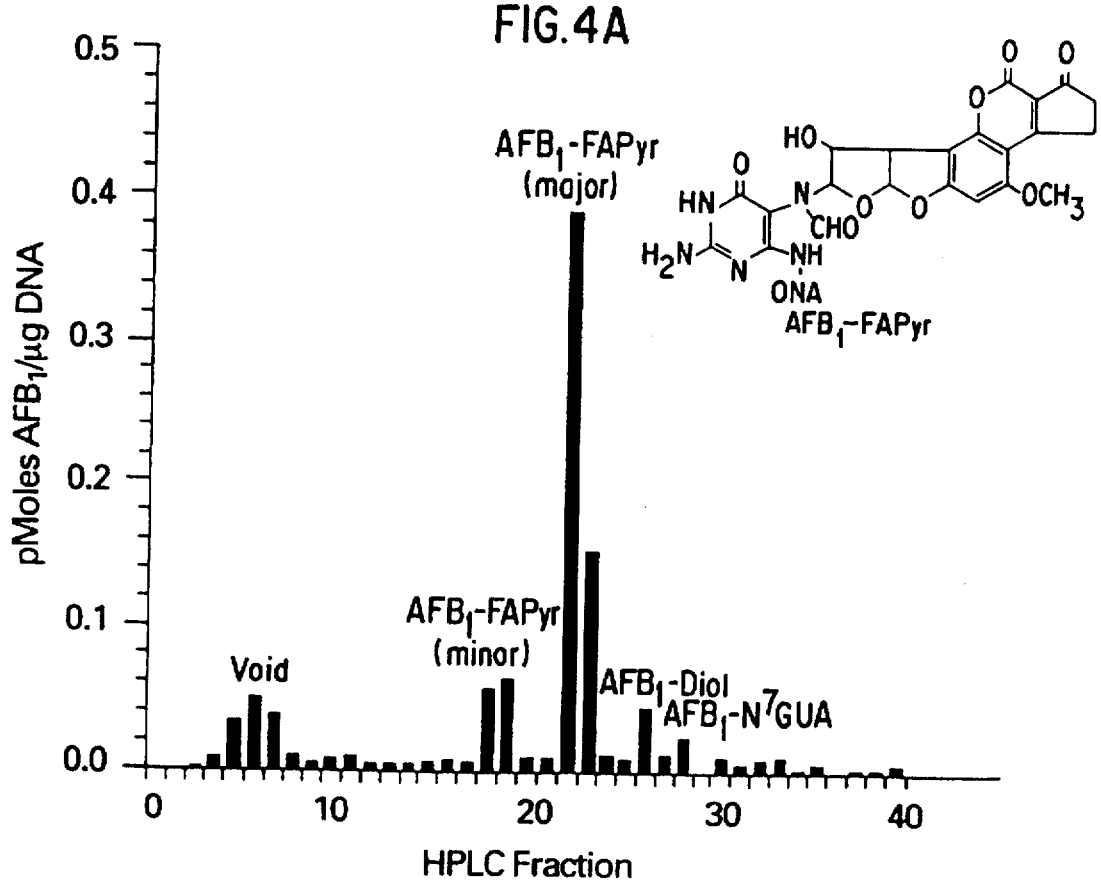
Figure 4B:
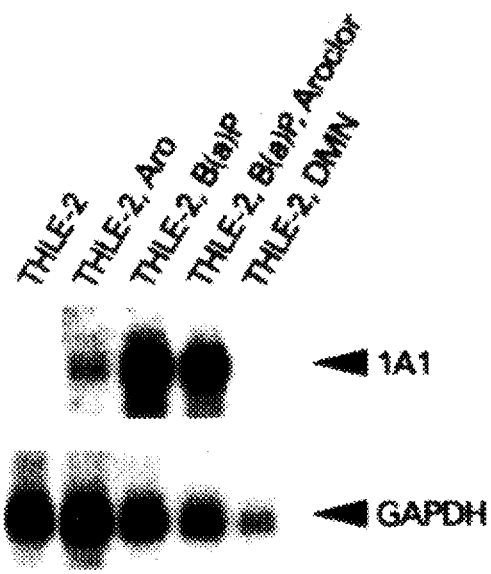
Figures 4C, 4D:
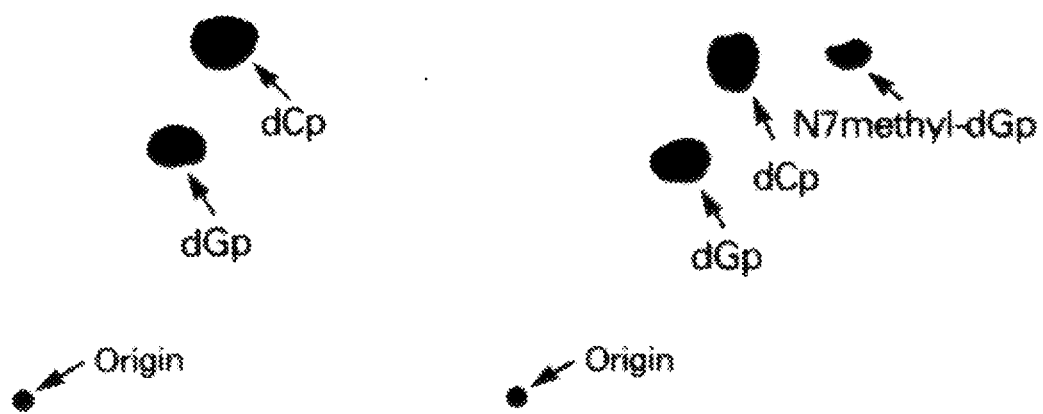

Albumin secretion from the THLE cells was assayed by Western blot analysis of immunoprecipitated albumin. Cell supernatants (10 ml from 72 hr cultures of approximately $0.6 \times 10^6$ cells/ml in flasks or $1.2 \times 10^6$ cells/ml in roller bottles, the cells were switched to LCM without conditioned medium 24 hours before the assay) were adjusted to the salt and detergent concentration of RIPA (1×) (40), the albumin immunoprecipitated (4° C.: 1 hr) with goat anti-human albumin (Dako, Santa Barbara, Calif.) and subjected to Western blot analysis and quantitative densitometry (FIG. 2). Albumin was isolated from cells grown in serum free medium for 24 hours in roller bottles (Rb) or flasks (Fl) ($0.6 \times 10^6$/ml respectively; 72 hrs) with 10 µl of goat anti-human albumin followed by extraction (1 hr) with protein A sepharose (Zymed, South San Francisco, Calif.). The immunocomplexes were washed twice with RIPA buffer, once in a mixture of equal volumes of RIPA and TNE (0.15M NaCl; 0.05M Tris-Hcl, pH 7.5; 1 mM EDTA) and once in TNE. The albumin protein was eluted in a sample buffer (200 µl, 0.06M Tris-HCl, ph 6.8, 2% SDS, 10% glycerol, 5% β-mercaptoethanol, 0.002% bromophenol blue), electrophoresed on a 7.5 SDS polyacrylamide gels and transferred to a nitrocellulose membrane. The membrane was blocked for nonspecific binding at room temperature (1 hr) with non-fat milk (5%) diluted in TBST (10 mM Tris, pH 7.5, 150 mM NaCl, 0.05% Tween 20) before hybridizing with a rabbit anti-human albumin antibody (Dako, Santa Barbara, Calif.) diluted 1:800 in TBST including 5% non-fat milk. Subsequently, the membrane was washed three times in TBST (10 min), incubated at room temperature with a swine anti-rabbit biotinylated antibody diluted 1:2000 in TBST (30 min), washed again as above and incubated at room temperature in streptavidin alkaline phosphatase in TBST (30 min) which generated a color reaction in the presence of the chromogen (ABComplex, Dako, Santa Barbara, Calif.).

Karyotype analysis of THLE-2 and THLE-3 cells shows that both lines are hypodiploid (aneuploid) with most karyotypes being near diploid. Each cell line's karyotype is distinctive; neither is completely normal. Both exhibit structural alterations such as chromatid breaks, deletions and acentric fragments. Both THLE-2 and THLE-3 have been tested for tumor formation by subcutaneous injection into athymic nude mice; no tumors have arisen after 12 months following injection of the cells.

Southern blot analysis of DNA from the THLE-2 cells shows that these cells contain a single copy of the SV40 T-antigen gene per haploid genome. Cultures of the SV40 TAg immortalized cells are passaged as mass cultures. Immunocytochemical analysis of both THLE-2 and THLE-3 cells between the 3rd and 5th passage shows that all of the cells of both lines express TAg in their nuclei.

At early passage (passage 3), both THLE-2 and THLE-3 cells demonstrate immunocytochemical evidence of expression of cytokeratin 18, but not cytokeratin 19. The early passage cells also stain positively for albumin. α-fetoprotein is not detectable by immunostaining. In situ hybridization to mRNA confirms the positive expression of albumin and lack of expression of α-fetoprotein. In situ hybridization also detects mRNA encoding transferrin, α2-macroglobulin and α-1-antitrypsin.

Re-examination of cytokeratin expression by immunostaining at passage 10 shows that both cytokeratin 18 and cytokeratin 19 are expressed at the later passage in both cell lines. Albumin expression in later passage cells (passage 12) is dependent upon culture conditions. Growth under conditions favoring rapid proliferation results in lower albumin expression. Growth under conditions which slow proliferation, such as roller bottle culture or plating on collagen or MATRIGEL™ surfaces results in increased albumin expression. Albumin secretion by THLE-2 cells in roller culture was approximately 300 pg/ml of culture medium. In flask culture, THLE-2 and THLE-3 cells produced 70 pg/ml and 14.5 ng/ml of albumin, respectively. Immunocytochemical analysis of albumin expression shows that albumin is readily detected in early passage THLE-2 an THLE-3 cells. Islands of cells staining for albumin were surrounded by clusters of less intensely staining cells, indicating the presence of different clonal types in the culture at low PDL.

THLE-2 cells have been evaluated for expression of a number of hepatocyte-specific markers. THLE-2 cells express cytokeratin 18 and not cytokeratin 19 at early passage, while at later passage, expression of both of these cytokeratins is observed. Since cytokeratin 19 is not normally expressed in vivo in hepatocytes, but is expressed in bile duct cells, this is an indication that the THLE cell lines either dedifferentiate toward a more primitive, less committed cell type during passage or that a stem cell type gains a selective advantage in the culture. Evidence that bile ductal cells and hepatocytes arise from a common stem cell has recently been shown by others (44).

Cells for γ-GT staining were plated onto coated glass chamber slides, washed in PBS, fixed in ice-cold acetone (2 min), and stored at −20° C. until used. Enzyme histochemical reaction for γ-GT was performed as described (41). The HepG2 cell line was used as a positive control and the hamster embryonic cell line 3T6 as a negative control. γ-GT was weakly detected by immunocytochemistry in some colonies of THLE-2 and THLE-3, as well as in primary cultures prior to viral transformation. 3T6 cells were negative, whereas HepG2 cells uniformly exhibited high levels of the enzyme.

For Factor VIII analysis, cells were fixed in ice-cold acetone (2 min) and incubated with a mouse monoclonal antibody to human factor VIII (45 min; Zymed) at room temperature. Primary cultures of human umbilical cord endothelial cells were used as a positive control. Factor VIII expression was not detected at early or late passage in THLE cells.

Expression of catalase, superoxide dismutase and glutathione peroxidase is evaluated in THLE-2 cells by Northern blot analysis. The cells are shown to express mRNA for each of these proteins.

When evaluated for mRNA expression, early passage THLE-2 cells are found to express messages for albumin, transferrin, α-1 antitrypsin, α2-macroglobulin, catalase, superoxide dismutase and glutathione peroxidase. α-fetoprotein expression is not detectable at either the mRNA or protein level. α-fetoprotein is not normally expressed by mature hepatocytes, but is secreted by regenerating liver and often by hepatocellular carcinoma. Thus, THLE-2 cells demonstrate a pattern of gene expression similar to that of normal hepatocytes in vivo. This pattern of gene expression indicates that cultures of THLE-2 cells (and probably THLE-3 cells, though they are not as well characterized) are mostly a dividing population of liver cells which maintain at least a partially differentiated phenotype.

Early passage THLE-2 and THLE-3 cells formed colonies with mixed ability to secrete albumin. We hypothesize that these cells constitute dedifferentiated hepatocytes that have varying ability to express albumin or arose from liver stem cells differentiated to cells with hepatocyte characteristics. In rats treated with hepatic carcinogens or toxic compounds, oval cells that are much smaller than parenchymal hepatocytes or nodular cells are observed (42–45). Oval cells can differentiate to liver parenchymal cells under particular conditions in vivo (43,45,46) suggesting that these cells may be stem cells with the potential of being neoplastically transformed to cholangiocellular, as well as hepatocellular carcinomas (44). Rat oval cells are characterized by the expression of phenotypic markers such as albumin, cytokeratin 18 and 19, γ-GT, α-fetoprotein and glutathione-S-transferase pi, whereas 6-glucose phosphatase activity is only weakly positive (43,45). THLE cells have an epithelial morphology; early passage cells secreted albumin, expressed cytokeratin 18, transferrin, $\alpha_1$-antitrypsin, α-macroglobulin, GST (FIGS. 1 and 2), and very low levels of γ-GT. They were uniformly negative for α-fetoprotein and factor VIII. Therefore, THLE cells represent a population with a differentiation grade between oval cells and hepatocytes. The possibility that the THLE cells are derived from hepatocyte precursors such as oval cells cannot be ruled out. However, the fact that cytokeratin 18 is expressed and α-fetoprotein is absent in a very early stage of their establishment indicates a derivation from differentiated hepatocytes rather than oval cells. The appearance of cytokeratin 19 and the decrease in albumin secretion at later passages suggests that the cells dedifferentiate in culture, a process often seen as a consequence of transformation (47). In the in vitro model of normal liver epithelial cells described here, dedifferentiation is reversible because albumin expression can be induced in roller bottles and by growing cells on extracellular matrices or in tridimensional aggregates.

A second consequence of dedifferentiation of hepatocytes is the loss of drug metabolizing enzymes including cytochrome P-450 and associated mixed-function oxidases (48). Culture conditions such as extracellular matrices (49–51), co-culture systems (43,52) and hormone supplementation (7,53,54) have been reported to positively influence differentiated functions including phase I and II enzyme activities of primary hepatocytes (50,55). Although SV-40 immortalized rat liver cell lines have not been extensively characterized for their metabolic potential, maintenance and/or inducibility of CYP2B and CYP1A, NADPH dytochrome P450 reductase, glutathione S-transferases and UDP-glucuronyltransferases with levels higher than in human or rat hepatoma cell lines have been reported (48). THLE cells expressed mRNAs of phase II enzymes such as epoxide hydrolase, CAT, GPD, SOD and GSTs at levels comparable to human liver. GST pi and α mRNAs are the dominant forms observed in both THLE cells and human liver, respectively. NADPH cytochrome P450 reductase was maintained but at a lower steady state mRNA level than in human liver.

EXAMPLE 3

Carcinogen Metabolism by THLE Cell Lines, DNA Adduct Formation

Metabolism of three carcinogen precursor compounds to form DNA adducts was evaluated in the THLE cell lines. Benzo-[a]-pyrene was used as a prototype compound of the polycyclic aromatic hydrocarbon class of carcinogen precursors. Similarly dimethylnitrosamine served as the prototype for the N-nitrosoamine class of carcinogen precursors and aflatoxin $B_1$ serves the prototype for the microtoxins, which are compounds made by microorganisms that have been shown to be metabolized by the mammalian liver to carcinogenic compounds.

For some experiments, one-half of the cultures are maintained in MLCM. The remainder of the cultures are treated with 10 μg/ml of Arochlor 1254 (NCI Chemical Repository, Kansas City, Mo.) twenty-four hours prior to incubation with either tritiated benzo-a-pyrene (B[a]P) or tritiated aflatoxin $B_1$ ($AFB_1$). In other experiments, the experimental cultures are treated with [$^3$H]-B[a]P, [$^3$H]-AFB1 or [$^3$H]-dimethylnitrosamine (DMN) for 24 hours without prior Arochlor treatment. Cells are isolated by trypsinization and pelleted by centrifugation at 200×g for 5 minutes. The supernatant is discarded and the cell pellet is resuspended in 5–10 ml of lysis buffer (Applied Biosystems, Foster City, Calif.). The lysis solution is incubated in RNAse for 2 hours, followed by a 2 hour treatment with proteinase K. DNA is purified from the lysis mixture by ethanol precipitation from the aqueous solution following chloroform/phenol extraction.

Purified AFB1-adducted DNA, re-dissolved in water, is adjusted of 0.15N HCl and incubated for 15 minutes at 90°–95 ° C., as described previously (Groopman et al. (23). This procedure releases greater than 95.5% of the covalently bound aflatoxins from the modified DNA. The hydrolysates are rapidly cooled on ice and adjusted to pH 5.3 with 1M ammonium formate. High performance liquid chromatography (HPLC) grade methanol is added to a final concentration of 5% and the samples are placed on a C-18 Sep-Pak column (Waters Assoc., Milford, Mass.), washed with 5% methanol in water to remove unhydrolyzed DNA and then eluted with 80% methanol in water. Subsequently, the solvent is removed from the eluate by rotary evaporation under reduced pressure to a 200–300 μl sample size for standard HPLC analysis (23).

DMN-DNA adduct analysis is performed with a combined HPLC and $^{32}$P-postlabelling assay as previously reported (24). Briefly, 100 μg of DNA is enzymatically digested to 3'-monophosphate nucleotides and then purified with ion-pair, reverse phase HPLC. Fractions containing N7-methyldeoxyguanosine (N7medGp) are mixed with deoxyguanosine (dGp) as an internal standard in the presence of polynucleotide kinase and 32P-gamma-ATP. Radioactive orthophosphates are thereby transferred to unmodified and adducted nucleotides. These are resolved and quantitated using two-dimensional thin layer chromatography, autoradiography and scintillation counting.

Analysis of B[a]P-DNA (BPDE-DNA) adducts is performed as previously described. Briefly, the DNA is hydrolyzed with DNAse I, alkaline phosphatase and phosphodiesterase and then mixed with UV-absorbing quantities of authentic BPDE-DNA adducts. The mixtures are applied to Sephadex LH20 columns (90 cm×5 cm, Pharmacia LKB, Piscataway, N.J.) and eluted with water-methanol gradients (30–100% over 1 liter). Fractions (5 ml) are analyzed for fluorescence emission (excitation 340 nm, emission 400 nm) and portions (1 ml) of each are subjected to liquid scintillation counting. Fractions containing radioactive and fluorescent materials are further characterized by HPLC for confirmation of adduct identity.

THLE-2 cells exposed to dimethylnitrosamine, aflatoxin B1 and benzo-[a]-pyrene show a dose-dependent cytotoxicity, suggesting that these cells have the ability to metabolize these compounds to genotoxic metabolites. Therefore, the formation of DNA adducts by these metabolites is investigated using THLE-2 and THLE-3 cells cultured in flasks or in roller bottles. The results of such studies are summarized in Table 2 and FIG. 5. Roller bottle cultures of both THLE-2 and THLE-3 cells demonstrate higher levels of adduct formation than the level observed in cells grown in flasks. No metabolism of AFB1 or B[a]P by THLE-2 cells is detectable when the cultures are maintained in flasks. However, both of these carcinogens are readily metabolized by cells incubated in roller bottle cultures. Metabolism of AFB1 by THLE-3 cells is similar to that observed in THLE-2 cells. However, metabolism of B[a]P to DNA-binding electrophiles by THLE-3 is independent of the vessel in which the culture is maintained.

Figure 5A:
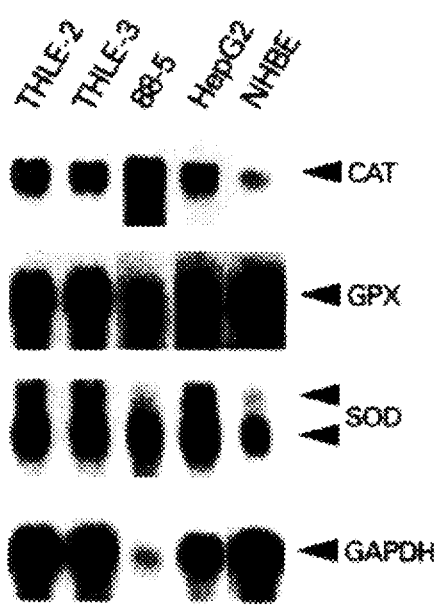
FIGS. 5A and B show Northern blot analysis of phase-II enzymes. Total RNA was isolated from THLE cells, normal human liver tissue, case 88-5, which led to the establishment of THLE-2, the hepatoblastoma cell line, HepG2, and normal human bronchial epithelial cells (NHBE). Based on ethidium bromide staining (GAPDH underestimated the amount of RNA loaded from the liver) similar expression of epoxide hydrolase (A), GPX, SOD (B) were found in THLE cells and human liver, whereas the expression of CAT (A) and cytochrome P450 reductase (B, NADPH-red.) was reduced.
Figure 5B:
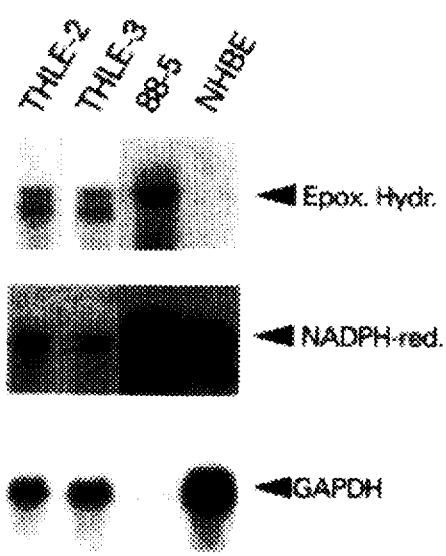

The p450-inducing agent Arochlor significantly increases the rate of adduct formation by B[a]P, but has no effect on AFB1 adduct formation. The increase in DNA adduct formation by Arochlor treatment is paralleled by induction of cytochrome p450 1A1 mRNA (FIG. 5). In cells not treated with Arochlor, cytochrome p450 1A1, and other p450 enzymes are not detectable under the culture conditions described. The metabolism of the parent B[a]P compound to the reactive electophile involves the action of either of two cytochrome p450 enzymes (P4501A1 and P450IIIA4) as well as the phase II biotransformation enzyme epoxide hydrolase (14). The amount of B[a]P dihydrodiol epoxide adduct found following exposure of THLE-2 cells to B[a]P indicates that at least one of the P450 enzymes as well as epoxide hydrolase are active and regulated by Arochlor 1254. Since Arochlor 1254 has been shown to induce the enzymatic activity of several forms of P450 in vivo (25), both of the THLE-2 and THLE-3 cell lines respond to such treatment in a physiologically relevant manner.

The results of the carcinogen metabolism studies are shown in Table I.

TABLE I

Carcinogen-DNA adducts formed in THLE-2 cells

| compound | uniduced | Arochlor-induced |
|---|---|---|
| B[*]P | 1.5 ± 0.1[b] | 4.9 ± 2.1 |
| AFB$_1$ | 2.5 ± 0.9 | 1.6 ± 0.4 |
| DMN | 30.4 ± 3.9 | 3.4 ± 0.1 |

[a]DNA isolated from cells treated with the vehicle only were negative for adducts of the carcinogens examined.
[b]mean ± standard deviation; fmol per μg DNA; each value given is calculated from two separate experiments, each having one observation.

The invention being thus described, various modifications of the materials or methods set forth will be apparent to one of skill in the art. Such variations in the scope of the invention are to be understood as encompassed by the invention as claimed below.

REFERENCES

The following references are cited above. Each is hereby incorporated in its entirety by such citation.
1. M. E. Kaighn and A. M. Prince, *Proc. Natl. Acad. Sci. USA* 68: 2396 (1971).
2. T. Sao et al., *Exp. Cell Res.* 154: 38 (1984).
3. R. Enat et al., *Proc. Natl. Acad. Sci. USA* 81: 1411 (1984).
4. J. F. Lechner et al., *Cancer Detect. Prev.* 14: 239 (1989).
5. C. C. Harris, *Cancer Res.* 47: 1 (1987).
6. D. E. Brash et al., *Somatic Cell Mol. Genet.* 13: 429 (1987).
7. C. D. Woodworth et al., *Cancer Res.* 46: 4018 (1986)
8. C. D. Woodworth and H. C. Isom, *Mol Cell Biol.* 7: 3740 (1987).
9. F. D. Ledley et al., *Proc. Natl. Acad. Sci. USA* 84: 5335 (1987)
10. J. F. Lechner et al., *Proc. Natl. Acad. Sci. USA* 82: 3884 (1985)
11. I. C. Hsu et al., *In Vitro Cell Develop. Biol.* 21: 154 (1985)
12. P. S. Jat et al., *Mol. Cell. Biol.* 6: 1204 (1986).
13. Y. Ke et al., *Am. J. Pathol.* 137: 833 (1990)
14. A. H. Conney, *Cancer Res.* 42: 4875 (1982)
15. U. Kasid, et al., *Science* 234: 1034 (1989)
16. R. Maier et al., *Mol. Cell. Endocrinol.* 82: 191 (1991); G. E. Lyons et al., *J. Cell Biol.* 111: 1465 (1990)
17. D. A. Melton et al., *Nucleic Acids Res.* 12: 7035 (1984).
18. P. Amstad et al., *Biochemistry* 30: 9305 (1991).
19. J. J. Dunn and F. W. Studier, *J. Mol. Biol.* 166: 477 (1983).
20. P. G. Board and G. C. Webb, *Proc. Natl. Acad. Sci. USA* 84: 2377 (1987).
21. R. M. Lawn et al., *Nucl. Acids. Res.* 9: 22 (1981).
22. R. Korneluh et al., *J. Biol. Chem.* 259: 13819 (1984).
23. D. Groopman et al., *Carcinogenesis* 13: 101 (1992).
24. A. Weston et al., *Chem. Biol. Interact.* 42: 233 (1982).
25. J. Eberhart et al., *Carcinogenesis* 13: 297 (1992).
26. W. H. Houser et al., *Mol. Carcinog.* 5: 232 (1992).
27. D. H. Swenson et al., *Biochem. Biophys. Res. Comm.* 60: 1036 1974).
28. S. DeFlora et al., *Mutat. Res.* 144: 213 (1985).
29. S. C. Strom et al., *J. Natl. Cancer Inst.* 68: 771 (1982).
30. H. S. Ramsdell et al., *Toxicol. Appl. Pharmacol.* 108: 436 (1991).
31. L. M. Forrester et al., *Proc. Natl. Acad. Sci. USA* 87: 8306 (1990).
32. H. Autrup et al., *Chem. Biol. Interact.* 50: 15 (1984).
33. S. C. Strom et al., in "The Isolated Hepatocyte: Use in Toxicology and Xenobiotic Biotransformation", pp. 265–280, E. J. Rauckman and G. M. Padilla, eds., c. 1987 by Academic Press, NY.
34. K. E. Cole et al., *Carcinogenesis* 10: 139 (1989).
35. K. E. Cole et al., *Carcinogenesis* 9: 711 (1988).
36. K. E. Cole et al., *Cancer Res.* 46: 1290 (1986).
37. I. C. Hsu et al., *Mutat. Res.* 177: 1 (1987).
38. G. H. Degen and H. G. Neumann, *Carcinogenesis* 2: 299 (1981).
39. A. Weston et al., *Proc. Natl. Acad. Sci. USA* 86: 5099 (1989).
40. T. Finkel et al., *Cell* 37: 151 (1984).
41. A. M. Rutenberg et al., *J. Histochem. Cytochem.* 17: 517 (1969).
42. N. Fausto et al., *Cell Separation Methods* 4: 45 (1987).
43. R. P. Evarts et al., *Cancer Res.* 49: 1541 (1989).
44. S. Sell, *Cancer Res.* 50: 3811 (1990).
45. Y. Ianoka, *Gann* 58: 355 (1967).
46. K. Ogawa et al., *Cancer Res.* 34: 3379 (1974).
47. G. C. Yeoh et al., *Cancer Res.* 50: 7593 (1990).
48. J. Bayad et al., *Biochem. Pharmacol.* 42: 1345 (1991).
49. C. M. DiPersio et al., *Mol. Cell. Biol.* 11: 4405 (1991).
50. R. E. Kane et al., *In Vitro Cellular and Developmental Biology* 27A: 953 (1991).
51. J. C. Dunn et al., *J. Cell Biol.* 116: 1043 (1992).
52. C. Guguen-Guillouzo et al., *Ex. Cell Res.* 143: 47 (1983).
53. J. Dich et al., *Hepatology* 8: 39 (1988).
54. J. Watanabe et al., *J. Histochem Cytochem.* 37: 1257 (1989).
55. D. Utesch et al., *In Vitro Cellular Developmental Biology* 27A: 858 (1991).

What is claimed is:

1. A continuous epithelial cell line isolated from normal adult human liver tissue consisting of cells which have the following characteristics:

1) the cells are immortalized by transformation with a virus selected from the group consisting of SV40 virus, adenovirus, and papilloma virus;

2) the cells metabolically activate carcinogen precursor compounds to DNA-adduct forming compounds;

3) the cells demonstrate a pattern of gene expression, wherein said pattern of gene expression is such that the cells:

a) do not express α-fetoprotein; and
   b) express mRNA encoding at least one of the proteins selected from the group consisting of a transferrin, α-1-antitrypsin, α2 macroglobulin, a catalase, superoxide dismutase and glutathione peroxidase; and 4) the cells are non-tumorigenic.

2. An epithelial cell line according to claim 1, wherein said precursor compound is benzo-[a]-pyrene.

3. The cell line of claim 1, wherein said cells also express cytokeratin 18 protein.

4. The cell line of claim 3, wherein said cells also express at least one cytochrome P450 in an inducible manner.

5. The cell line of claim 1, wherein said cells also express at least one cytochrome P450 in an inducible manner.

6. The cell line of claim 1, wherein said cells have the further characteristic of increasing albumin expression when cultured in roller bottle culture or on a collagen surface.

7. The cell line of claim 1, wherein said cells can be reversibly dedifferentiated.

8. A continuous human liver epithelial cell line isolated from normal adult human liver tissue consisting of cells having the following characteristics:

1) the cells have been immortalized by transformation with SV40 T antigen;

2) the cells metabolically activate carcinogen precursor compounds to DNA-adduct forming compounds;

3) the cells demonstrate a pattern of gene expression, wherein said pattern of gene expression is such that the cells:
   a) do not express α-fetoprotein; and
   b) express mRNA encoding at least one of the proteins selected from the group consisting of a transferrin, α-1-antitrypsin, α2 macroglobulin, a catalase, superoxide dismutase and glutathione peroxidase; and 4) the cells are non-tumorigenic.

9. The cell line of claim 8, wherein said cells can be reversibly dedifferentiated.

10. The cell line of claim 8, wherein said cells have the further characteristic of increasing albumin expression when cultured in roller bottle culture or on a collagen surface.

11. A continuous human liver epithelial cell line isolated from normal adult human liver tissue consisting of cells having the following characteristics:
   1) the cells have been immortalized by transformation with the transforming genes of a transforming virus selected from the group consisting of SV40 virus, adenovirus, and papilloma compounds to DNA-adduct forming compounds;

2) the cells metabolically activate carcinogen precursor compounds to DNA-adduct forming compounds;

3) the cells demonstrate a pattern of gene expression, wherein said pattern of gene expression is such that the cells:
      a) do not express α-fetoprotein; and
      b) express mRNA encoding at least one of the proteins selected from the group consisting of a transferrin, α-1-antitrypsin, α2 macroglobulin, a catalase, superoxide dismutase and glutathione peroxidase; and 4) the cells are non-tumorigenic.

12. The cell line of claim 11, wherein said transforming genes are the E1A and E1B genes of adenovirus or the E6 and E7 genes of papilloma virus.

13. The cell line of claim 11, wherein said transforming genes are the E6 and E7 genes of papilloma virus.

14. The cell line of claim 11, wherein said cells have the further characteristic of increasing albumin expression when cultured in roller bottle culture or on a collagen surface.

15. The cell line which is the THLE-3 (ATCC CRL 11233) cell line.

* * * * *